United States Patent
Jensen et al.

(10) Patent No.: US 12,137,887 B2
(45) Date of Patent: Nov. 12, 2024

(54) SAMPLE CONTAINER AND COAXIAL INTRODUCER CANNULA FOR A BIOPSY APPARATUS

(71) Applicant: C. R. Bard, Inc., Franklin Lakes, NJ (US)

(72) Inventors: Angela K. Jensen, Phoenix, AZ (US); Søren F. Ørts, Virum (DK); Jens J. Holme, Lyngby (DK)

(73) Assignee: C. R. Bard, Inc., Franklin Lakes, NJ (US)

( * ) Notice: Subject to any disclaimer, the term of this patent is extended or adjusted under 35 U.S.C. 154(b) by 327 days.

(21) Appl. No.: 16/764,966

(22) PCT Filed: Nov. 29, 2018

(86) PCT No.: PCT/US2018/063055
§ 371 (c)(1),
(2) Date: May 18, 2020

(87) PCT Pub. No.: WO2019/108786
PCT Pub. Date: Jun. 6, 2019

(65) Prior Publication Data
US 2020/0345335 A1    Nov. 5, 2020

Related U.S. Application Data

(60) Provisional application No. 62/592,641, filed on Nov. 30, 2017, provisional application No. 62/669,015, filed on May 9, 2018.

(51) Int. Cl.
*A61B 10/02* (2006.01)
*A61B 10/00* (2006.01)

(52) U.S. Cl.
CPC ...... *A61B 10/0283* (2013.01); *A61B 10/0096* (2013.01); *A61B 10/0275* (2013.01); *A61B 2010/0208* (2013.01)

(58) Field of Classification Search
CPC combination set(s) only.
See application file for complete search history.

(56) References Cited

U.S. PATENT DOCUMENTS 3,757,891 A    9/1973    Krieger
3,800,783 A    4/1974    Jamshidi
(Continued)

FOREIGN PATENT DOCUMENTS

CN    101297764 A    * 11/2008    ......... A61B 10/0096
CN    102018537 A    *  4/2011    ......... A61B 10/0096
(Continued)

OTHER PUBLICATIONS

Office Action dated Jan. 28, 2023 pertaining to Chinese Patent Application 201880077285.5.

*Primary Examiner* — Sean P Dougherty
(74) *Attorney, Agent, or Firm* — Dinsmore & Shohl LLP

(57) ABSTRACT

A biopsy apparatus includes a biopsy needle, a sample manifold, and a sample container. The sample manifold is coupled to the biopsy needle. The sample manifold has a receptacle and an insertion axis. The sample receptacle has an interior side wall and a mounting pin that projects inwardly from the interior side wall toward the insertion axis. The sample container is configured for insertion into the receptacle. The sample container includes a cap portion, a basket portion, and a hinge, wherein the cap portion is joined to the basket portion by the hinge.

13 Claims, 10 Drawing Sheets

(56) References Cited

U.S. PATENT DOCUMENTS

| | | | |
|---|---|---|---|
| 3,929,123 A | 12/1975 | Jamshidi | |
| 4,517,965 A | 5/1985 | Ellison | |
| 4,909,782 A | 3/1990 | Semm et al. | |
| 4,940,061 A | 7/1990 | Terwilliger et al. | |
| 5,031,634 A | 7/1991 | Simon | |
| 5,125,521 A | 6/1992 | Somogyi | |
| 5,148,813 A | 9/1992 | Bucalo | |
| 5,201,716 A | 4/1993 | Richard | |
| 5,284,156 A | 2/1994 | Schramm et al. | |
| 5,400,798 A | 3/1995 | Baran | |
| 5,421,819 A | 6/1995 | Edwards et al. | |
| 5,507,298 A | 4/1996 | Schramm et al. | |
| 5,634,918 A | 6/1997 | Richards | |
| 5,794,626 A | 8/1998 | Kieturakis | |
| 5,817,033 A | 10/1998 | Desantis et al. | |
| 5,857,981 A | 1/1999 | Bucalo et al. | |
| 5,959,433 A | 9/1999 | Rohde | |
| 6,126,617 A | 10/2000 | Weilandt et al. | |
| 6,171,261 B1 * | 1/2001 | Niermann | A61B 10/0096 600/573 |
| 6,273,862 B1 | 8/2001 | Privitera et al. | |
| 6,312,429 B1 | 11/2001 | Burbank et al. | |
| 6,416,484 B1 | 7/2002 | Miller et al. | |
| D463,555 S | 9/2002 | Etter et al. | |
| 6,497,706 B1 | 12/2002 | Burbank et al. | |
| 6,551,253 B2 | 4/2003 | Worm et al. | |
| 6,702,761 B1 | 3/2004 | Damadian et al. | |
| D491,268 S | 6/2004 | Hickingbotham | |
| D497,427 S | 10/2004 | Hickingbotham | |
| 6,870,475 B2 | 3/2005 | Fitch et al. | |
| 6,872,185 B2 | 3/2005 | Fisher | |
| 6,875,183 B2 | 4/2005 | Cervi | |
| D535,748 S | 1/2007 | Wolf | |
| 7,189,206 B2 | 3/2007 | Quick et al. | |
| 7,252,641 B2 | 8/2007 | Thompson et al. | |
| 7,344,507 B2 | 3/2008 | Briggs et al. | |
| 7,456,606 B1 | 11/2008 | Legg | |
| 7,470,237 B2 | 12/2008 | Beckman et al. | |
| 7,488,295 B2 | 2/2009 | Burbank et al. | |
| 7,495,359 B2 | 2/2009 | Klinke et al. | |
| 7,762,961 B2 | 7/2010 | Heske et al. | |
| 7,866,412 B2 | 1/2011 | Avis | |
| 7,952,322 B2 | 5/2011 | Partovi et al. | |
| D643,531 S | 8/2011 | van der Weiden | |
| 8,002,732 B2 | 8/2011 | Visconti | |
| 8,118,755 B2 | 2/2012 | Hibner et al. | |
| 8,169,185 B2 | 5/2012 | Partovi et al. | |
| 8,192,369 B2 | 6/2012 | Bacon et al. | |
| 8,197,419 B2 | 6/2012 | Field et al. | |
| 8,207,906 B2 | 6/2012 | Tiscareno et al. | |
| 8,282,321 B2 | 10/2012 | Thiel | |
| 8,298,213 B2 | 10/2012 | Singh | |
| 8,333,782 B2 | 12/2012 | Creaven | |
| 8,413,811 B1 | 4/2013 | Arendt | |
| 8,454,532 B2 | 6/2013 | Hibner | |
| 8,480,595 B2 | 7/2013 | Speeg, V et al. | |
| 8,629,654 B2 | 1/2014 | Partovi et al. | |
| 8,696,674 B2 | 4/2014 | Howard et al. | |
| 8,702,623 B2 | 4/2014 | Parihar et al. | |
| 8,845,546 B2 | 9/2014 | Speeg et al. | |
| 8,845,548 B2 | 9/2014 | Hibner et al. | |
| 8,858,465 B2 | 10/2014 | Fiebig | |
| 8,864,682 B2 | 10/2014 | Hibner | |
| 8,968,212 B2 | 3/2015 | Speeg et al. | |
| 9,000,720 B2 | 4/2015 | Stulen et al. | |
| 9,072,506 B1 | 7/2015 | Seiger et al. | |
| 9,078,671 B2 | 7/2015 | Beale et al. | |
| 9,101,347 B2 | 8/2015 | Mcghie et al. | |
| 9,107,691 B2 | 8/2015 | Fojtik | |
| 9,149,598 B2 | 10/2015 | Dugan et al. | |
| 9,155,527 B2 | 10/2015 | Vetter et al. | |
| 9,178,369 B2 | 11/2015 | Partovi | |
| 9,381,058 B2 | 7/2016 | Houser et al. | |
| 9,392,998 B2 | 7/2016 | Snow | |
| 9,421,062 B2 | 8/2016 | Houser et al. | |
| 9,480,463 B2 | 11/2016 | Hibner et al. | |
| 9,486,184 B2 | 11/2016 | Hibner et al. | |
| 9,496,732 B2 | 11/2016 | Partovi | |
| 9,504,477 B2 | 11/2016 | Miller et al. | |
| 9,566,045 B2 | 2/2017 | Videbaek et al. | |
| 9,585,639 B2 | 3/2017 | Swick et al. | |
| 9,603,587 B2 | 3/2017 | Fiebig et al. | |
| 9,655,639 B2 | 5/2017 | Mark | |
| 9,717,482 B2 | 8/2017 | Fiebig et al. | |
| D802,763 S | 11/2017 | Sweitzer | |
| 9,833,222 B2 | 12/2017 | Fiebig | |
| 9,872,694 B2 | 1/2018 | Chin | |
| 9,909,103 B2 | 3/2018 | Howard et al. | |
| 9,931,105 B2 | 4/2018 | Mark et al. | |
| 10,022,110 B2 | 7/2018 | Stand, III et al. | |
| 10,048,176 B2 | 8/2018 | Mark et al. | |
| RE47,148 E | 12/2018 | Rhad et al. | |
| 10,285,669 B2 | 5/2019 | Keller | |
| 11,382,308 B2 * | 7/2022 | Gardner | A61F 13/38 |
| 2004/0049128 A1 | 3/2004 | Miller et al. | |
| 2005/0113716 A1 | 5/2005 | Mueller, Jr. et al. | |
| 2006/0108977 A1 | 5/2006 | Kagermeier et al. | |
| 2006/0260994 A1 | 11/2006 | Mark | |
| 2009/0079386 A1 | 3/2009 | Gallagher et al. | |
| 2009/0171147 A1 | 7/2009 | Lee et al. | |
| 2009/0247901 A1 | 10/2009 | Zimmer | |
| 2010/0114031 A1 | 5/2010 | Jarial et al. | |
| 2010/0152611 A1 | 6/2010 | Parihar et al. | |
| 2010/0292607 A1 | 11/2010 | Moore et al. | |
| 2011/0017544 A1 | 1/2011 | Bodwell et al. | |
| 2011/0071432 A1 | 3/2011 | Carrillo, Jr. et al. | |
| 2011/0087131 A1 | 4/2011 | Karsten | |
| 2011/0262405 A1 * | 10/2011 | Segina | A61M 1/0001 604/319 |
| 2012/0065542 A1 | 3/2012 | Hibner et al. | |
| 2012/0152611 A1 | 6/2012 | Fisher et al. | |
| 2014/0191709 A1 | 7/2014 | Celentano et al. | |
| 2014/0275999 A1 | 9/2014 | Speeg et al. | |
| 2014/0276665 A1 | 9/2014 | Lopez et al. | |
| 2015/0065913 A1 * | 3/2015 | Keller | A61B 10/0283 600/566 |
| 2015/0088031 A1 | 3/2015 | Paronetto | |
| 2016/0038127 A1 | 2/2016 | Hashimshony | |
| 2016/0256137 A1 | 9/2016 | Snow | |
| 2016/0317133 A1 | 11/2016 | Orts et al. | |
| 2017/0333012 A1 | 11/2017 | Hathaway | |
| 2018/0000463 A1 * | 1/2018 | Keller | A61B 10/0283 |
| 2018/0055493 A1 | 3/2018 | Krueger et al. | |
| 2018/0098755 A1 * | 4/2018 | Keller | A61B 10/0096 |
| 2018/0153526 A1 | 6/2018 | Nock et al. | |

FOREIGN PATENT DOCUMENTS

| | | | |
|---|---|---|---|
| CN | 104797200 B | 4/2018 | |
| CN | 108348678 A * | 7/2018 | A61B 10/0283 |
| CN | 105705099 B | 7/2019 | |
| DE | 3917051 A1 | 12/1989 | |
| DE | 10050742 A1 | 4/2001 | |
| DE | 10064228 A1 | 6/2001 | |
| DE | 102008034085 A1 * | 1/2010 | A61B 10/0096 |
| EP | 0159492 A2 | 10/1985 | |
| EP | 0497973 A1 | 8/1992 | |
| EP | 0647121 A1 | 4/1995 | |
| EP | 0751744 A1 | 1/1997 | |
| EP | 1266624 A1 | 12/2002 | |
| EP | 1317211 A1 | 6/2003 | |
| EP | 1339326 A2 | 9/2003 | |
| EP | 1673015 A2 | 6/2006 | |
| EP | 1829487 A1 | 9/2007 | |
| EP | 1852070 A1 | 11/2007 | |
| EP | 1998685 A2 | 12/2008 | |
| EP | 2131745 A1 | 12/2009 | |
| EP | 2196153 A2 | 6/2010 | |
| EP | 2704636 A1 | 3/2014 | |
| EP | 2747666 A1 | 7/2014 | |
| EP | 2976019 A1 | 1/2016 | |
| EP | 2984991 A1 | 2/2016 | |
| EP | 2997902 A2 | 3/2016 | |
| EP | 3034008 A1 | 6/2016 | |

(56) References Cited

FOREIGN PATENT DOCUMENTS

| | | |
|---|---|---|
| EP | 3292822 A2 | 3/2018 |
| EP | 3308716 A1 | 4/2018 |
| EP | 3338646 A1 | 6/2018 |
| GB | 1116465 A | 6/1968 |
| GB | 1393068 A | 5/1975 |
| GB | 1450853 A | 9/1976 |
| WO | 9203096 A1 | 3/1992 |
| WO | 9314018 A1 | 7/1993 |
| WO | 9524858 A1 | 9/1995 |
| WO | 9613214 A1 | 5/1996 |
| WO | 9825522 A1 | 6/1998 |
| WO | 9835615 A1 | 8/1998 |
| WO | 9915079 A1 | 4/1999 |
| WO | 02062229 A2 | 8/2002 |
| WO | 02062232 A1 | 8/2002 |
| WO | 03079907 A1 | 10/2003 |
| WO | WO-2005087603 A1 * | 9/2005 ......... A61B 10/0096 |
| WO | 2006083770 A2 | 8/2006 |
| WO | 2006136588 A1 | 12/2006 |
| WO | 2007021903 A2 | 2/2007 |
| WO | 2007140846 A2 | 12/2007 |
| WO | 2009085821 A2 | 7/2009 |
| WO | 2010027554 A1 | 3/2010 |
| WO | 2013068017 A1 | 5/2013 |
| WO | 2013158072 A1 | 10/2013 |
| WO | 2013184466 A1 | 12/2013 |
| WO | WO-2013192606 A1 * | 12/2013 ......... A01N 1/0273 |
| WO | 2014068468 A1 | 5/2014 |
| WO | 2014123886 A2 | 8/2014 |
| WO | 2014129743 A1 | 8/2014 |
| WO | 2016053165 A1 | 4/2016 |
| WO | 2016178656 A1 | 11/2016 |
| WO | 2016196597 A1 | 12/2016 |
| WO | 2016198910 A1 | 12/2016 |
| WO | 2017035213 A1 | 3/2017 |
| WO | 2018098239 A1 | 5/2018 |
| WO | 2018127848 A1 | 7/2018 |
| WO | 2018148431 A1 | 8/2018 |

* cited by examiner

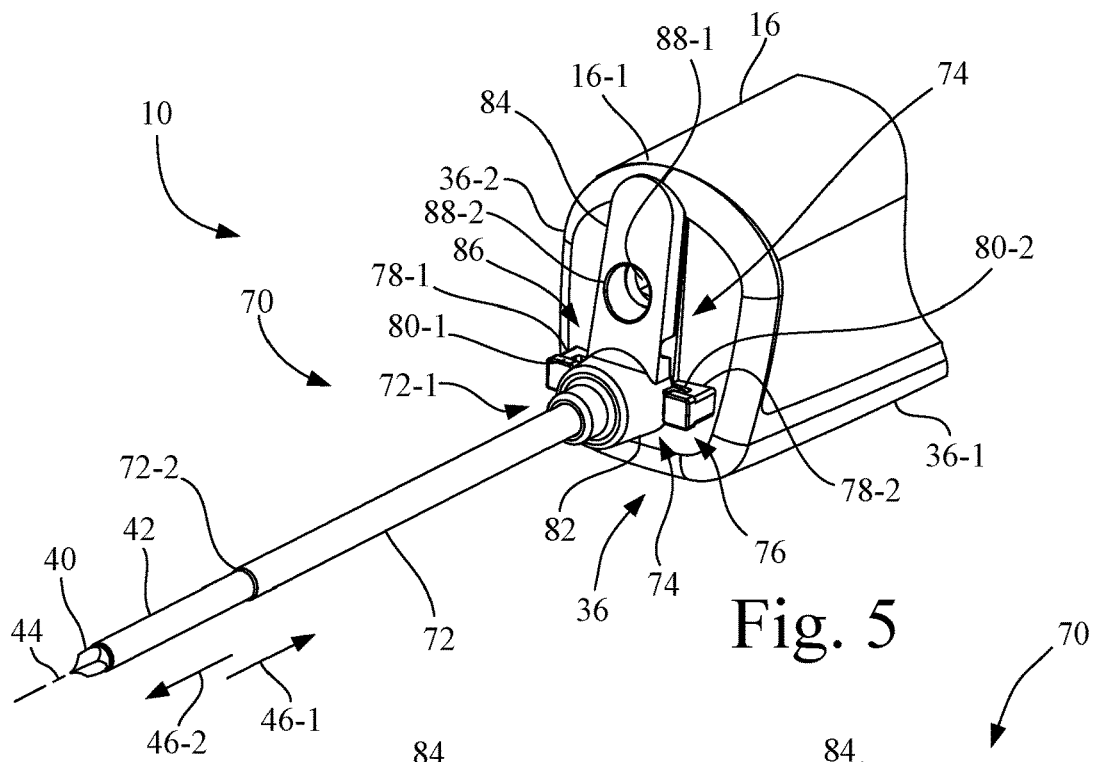
Fig. 5
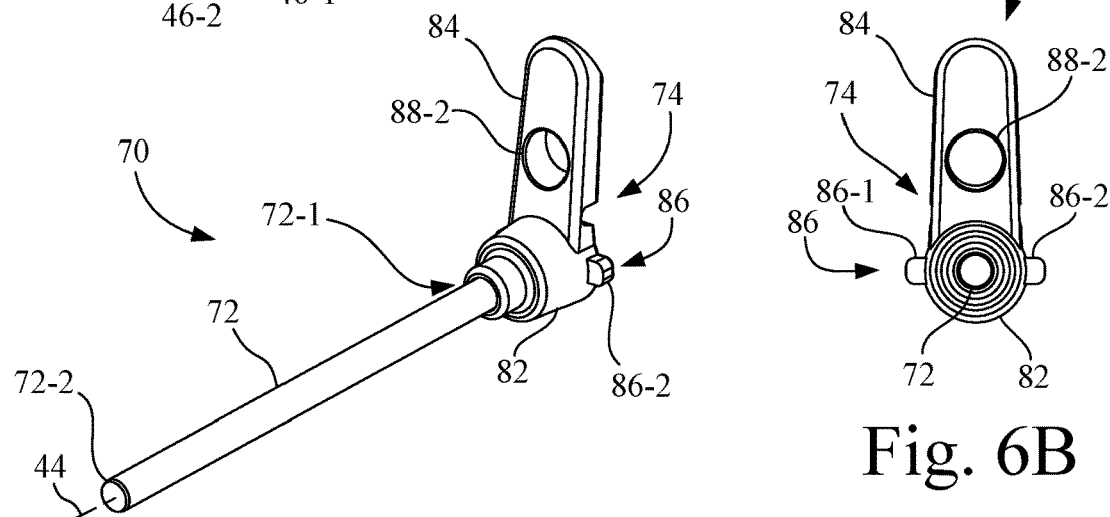
Fig. 6A
Fig. 6B
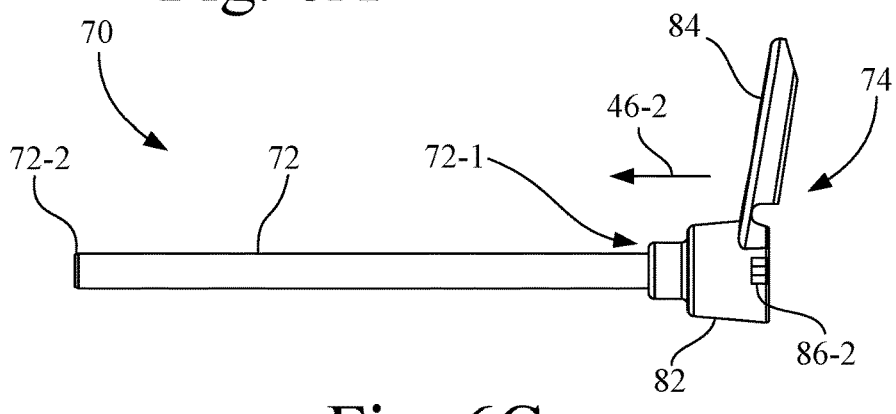
Fig. 6C

SAMPLE CONTAINER AND COAXIAL INTRODUCER CANNULA FOR A BIOPSY APPARATUS

CROSS-REFERENCE TO RELATED APPLICATIONS

This application is a U.S. national phase of International Application No. PCT/US2018/063055, filed Nov. 29, 2018, which claims priority to U.S. provisional patent application Ser. No. 62/592,641 entitled "SAMPLE CONTAINER AND COAXIAL CANNULA FOR BIOPSY APPARATUS" filed Nov. 30, 2017, and U.S. provisional patent application Ser. No. 62/669,015 entitled "SAMPLE CONTAINER FOR A SIMS BIOPSY DEVICE" filed May 9, 2018, which are incorporated herein by reference.

TECHNICAL FIELD

The present invention relates to a biopsy apparatus, and, more particularly, to a biopsy apparatus having a coaxial introducer cannula and/or sample container.

BACKGROUND ART

A biopsy may be performed on a patient to help in determining whether the tissue in a region of interest includes cancerous cells. One biopsy technique used to evaluate breast tissue, for example, involves inserting a biopsy probe into the breast tissue region of interest to capture one or more tissue samples from the region. Such a biopsy technique often utilizes a vacuum to pull the tissue to be sampled into a sample notch of the biopsy probe, after which the tissue is severed and collected in a sample container. Efforts continue in the art to improve the ability for a practitioner to access a biopsy site, and/or to transport the severed tissue sample to a sample container for collecting severed tissue samples.

For example, after performing a biopsy under ultrasound needle guidance, some operators may prefer not to handle the tissue specimens, and rather, may prefer to place the tissue specimens directly into formalin, which is a preservative for biological specimens. In contrast, other operators may require access to the tissue specimens for examination prior to placing in formalin. Also, when removing specimens with current devices, such as an open specimen tray, there may be a risk of specimen loss. In addition, anecdotal reports from physicians, including pathologists, suggest that tissue handling by the operators (physicians and technologists) during and after a biopsy procedure could impact the quality of the specimens for pathological analysis.

In addition, some operators may prefer to use a coaxial cannula to maintain an access path to the lesion when utilizing a biopsy apparatus, such as a biopsy driver coupled to a biopsy probe, or a trocar. In one such procedure, the operator may want to place a tissue marker at the biopsy site, in which case the biopsy probe may be withdrawn from the coaxial introducer cannula, and a marker applicator may be inserted through the coaxial introducer cannula to the biopsy site, so as to maintain the lesion/site position after sampling without having to re-target the lesion location using ultrasound. However, the connection and/or disconnection of the coaxial introducer cannula to the biopsy apparatus typically requires the use of two hands, and may be awkward or difficult.

What is needed in the art is a sample container for a biopsy apparatus that facilitates efficient reception and processing of collected tissue samples, and/or a coaxial introducer cannula that facilitates efficient connection and disconnection of the coaxial introducer cannula to the biopsy apparatus.

SUMMARY OF INVENTION

The present invention provides a sample container for a biopsy apparatus that facilitates efficient reception and processing of collected tissue samples, and/or a coaxial introducer cannula that facilitates efficient connection and disconnection of the coaxial introducer cannula to the biopsy apparatus.

The invention in one form is directed to a biopsy apparatus that includes a biopsy needle, a sample manifold, and a sample container. The sample manifold is coupled to the biopsy needle. The sample manifold has a receptacle and an insertion axis. The sample receptacle has an interior side wall and a mounting pin that projects inwardly from the interior side wall toward the insertion axis. The sample container is configured for insertion into the receptacle. The sample container includes a mounting channel that is sized and positioned to engage and follow the mounting pin of the receptacle as the sample container is rotated.

The invention in another form is directed to a coaxial introducer cannula for use with the biopsy apparatus. The biopsy apparatus has a front plate having a catch, and a biopsy needle extends from the front plate on a longitudinal axis. The coaxial introducer cannula includes a coaxial cannula and a hub. The coaxial cannula is sized to be coaxially and slidably received over the biopsy needle. The hub is fixedly attached to a proximal portion of the coaxial cannula. The hub has a hub body, a latching lever, and a latch. The latch is configured to rotatably engage the catch. The latching lever extends radially from the hub body relative to the longitudinal axis. The latching lever is longer than a height of the front plate so that the latching lever can be reached and rotationally operated to rotate the hub relative to the front plate of the biopsy apparatus, thereby facilitating single-handed rotation of the coaxial introducer cannula relative to the front plate, so as to effect a respective engagement or disengagement of the latch of the coaxial introducer cannula with the catch of the front plate.

One advantage of the sample container aspect of the present invention is that the sample container, in a closed position, may be removed from the biopsy apparatus and placed directly into formalin, without having to open the sample container or handle the tissue samples.

Another advantage of the sample container aspect of the present invention is that it provides an easy-to-use opening mechanism that allows for tissue access, if desired, but also will keep the sample container closed during removal from the biopsy system to help reduce the chance of tissue loss.

One advantage of the coaxial introducer cannula aspect of the present invention is that the operator is able to detach the coaxial introducer cannula from the biopsy apparatus with a single hand, improving the ease of use of the coaxial introducer cannula and the accuracy of any subsequent marker placement.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 5 is a perspective view of a portion of the biopsy apparatus of FIG. 1, with a coaxial introducer cannula in accordance with an aspect of the present invention mounted to the biopsy probe assembly of the biopsy apparatus;

FIG. 6A is a perspective view of the coaxial introducer cannula of FIG. 5;

FIG. 6B is an end view of the coaxial introducer cannula of FIG. 5;

FIG. 6C is a side view of the coaxial introducer cannula of FIG. 5;

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
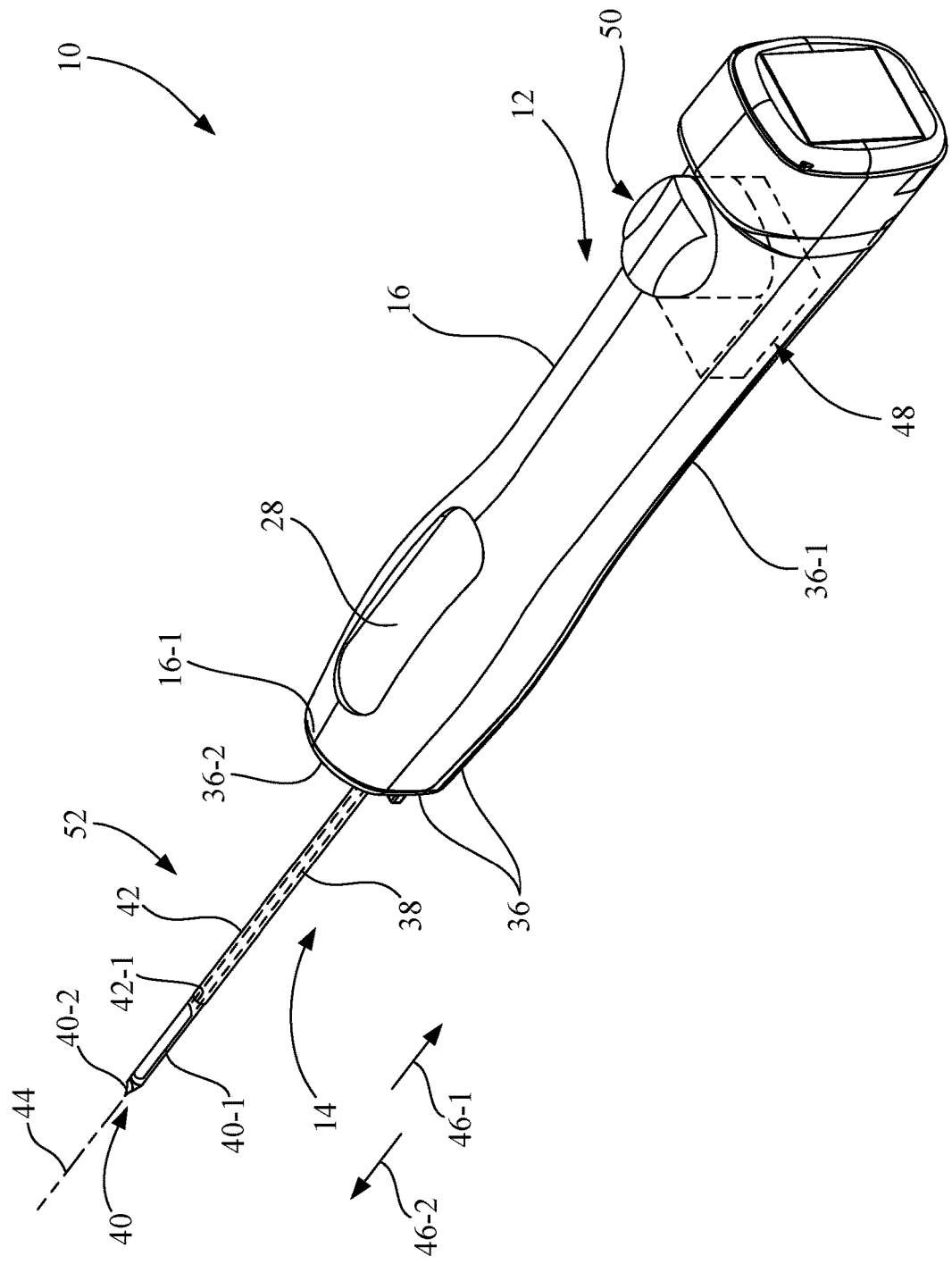
FIG. 1 is a perspective view of a biopsy apparatus having a sample container in accordance with an aspect of the present invention, and with a biopsy probe assembly attached to a driver assembly.

Referring now to the drawings, and more particularly to FIG. 1, there is shown a biopsy apparatus 10 which generally includes a non-invasive, e.g., non-disposable, driver assembly 12 and an invasive, e.g., disposable, biopsy probe assembly 14. As used herein, the term "non-disposable" is used to refer to a device that is intended for use on multiple patients during the lifetime of the device, and the term "disposable" is used to refer to a device that is intended to be disposed of after use on a single patient. Driver assembly 12 includes a driver housing 16 that is configured and ergonomically designed to be grasped by an operator.

Figure 2:
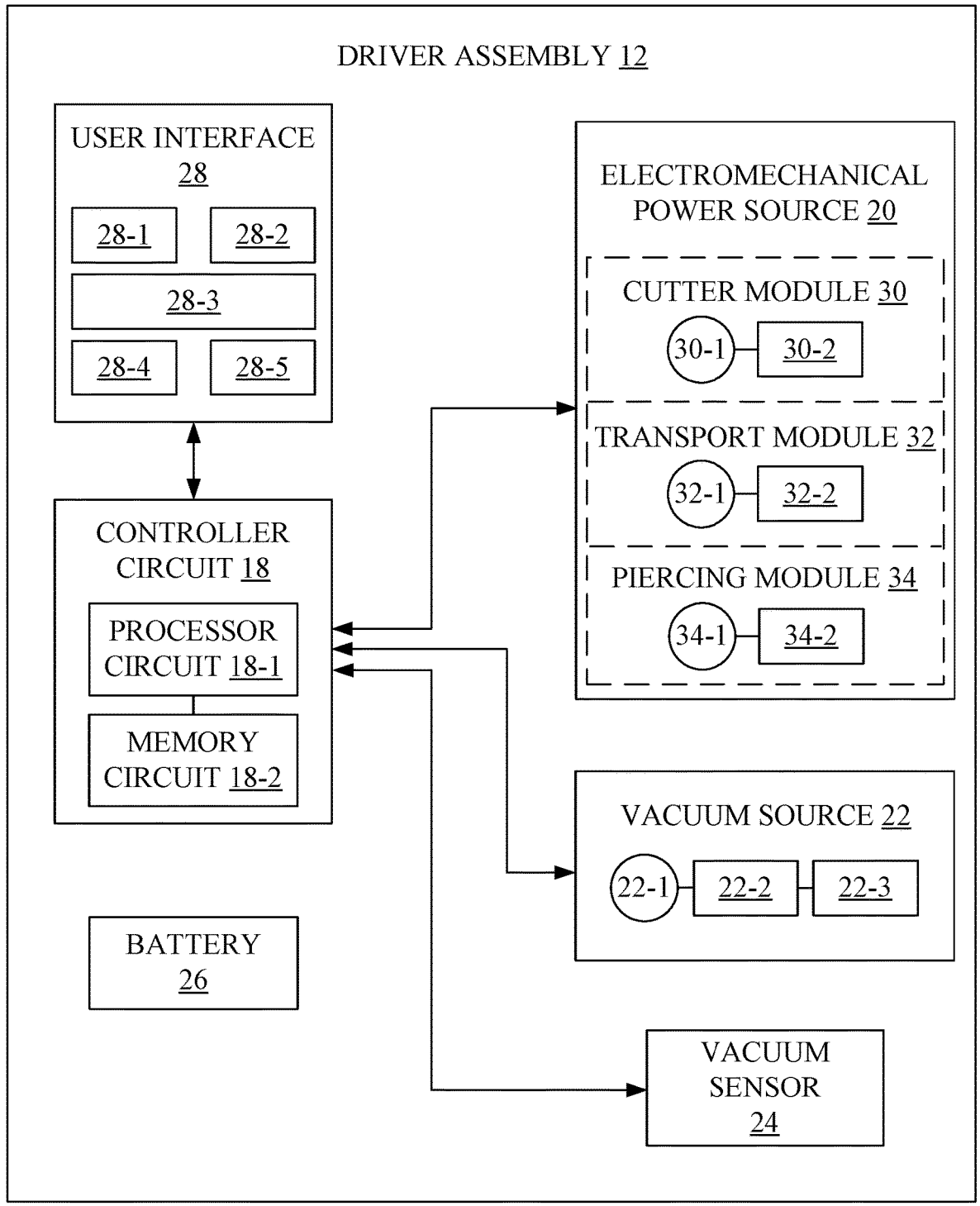
FIG. 2 is a block representation of the driver assembly of FIG. 1.

Referring also to FIG. 2, driver assembly 12 includes within driver housing 16 a controller circuit 18, an electromechanical power source 20, a vacuum source 22, a vacuum sensor 24, and a battery 26 (or alternatively an AC adapter). A user interface 28 (see FIG. 1), such as a keypad, is located to be mounted to driver housing 16, and externally accessible by the operator with respect to driver housing 16.

Battery 26 may be, for example, a rechargeable battery, which may be charged by an inductive charging device, or alternatively, by an electrical connection to an electrical power supply. Battery 26 is electrically coupled to controller circuit 18, electromechanical power source 20, vacuum source 22, and user interface 28.

User interface 28 may include control buttons and visual/aural indicators, with the control buttons providing user control over various functions of biopsy apparatus 10, and with the visual/aural indicators providing visual/aural feedback of the status of one or more conditions and/or positions of components of biopsy apparatus 10. The control buttons may include a sample button 28-1 and a prime/pierce button 28-2. The visual indicators may include a display screen 28-3 and/or one or more light emitting diodes (LED) 28-4. The aural indicator may include a buzzer 28-5. The control buttons may include tactile feedback to the operator when activated.

Controller circuit 18 is electrically and communicatively coupled to electromechanical power source 20, vacuum source 22, vacuum sensor 24, and user interface 28, such as by one or more wires or circuit traces. Controller circuit 18 may be assembled on an electrical circuit board, and includes, for example, a processor circuit 18-1 and a memory circuit 18-2.

Processor circuit 18-1 has one or more programmable microprocessors and associated circuitry, such as an input/output interface, clock, buffers, memory, etc. Memory circuit 18-2 is communicatively coupled to processor circuit 18-1, e.g., via a bus circuit, and is a non-transitory electronic memory that may include volatile memory circuits, such as random access memory (RAM), and non-volatile memory circuits, such as read only memory (ROM), electronically erasable programmable ROM (EEPROM), NOR flash memory, NAND flash memory, etc. Controller circuit 18 may be formed as one or more Application Specific Integrated Circuits (ASIC).

Controller circuit 18 is configured via software and/or firmware residing in memory circuit 18-2 to execute program instructions to perform functions associated with the retrieval of biopsy tissue samples, such as that of controlling and/or monitoring one or more components of electromechanical power source 20, vacuum source 22, and vacuum sensor 24.

Electromechanical power source 20 may include, for example, a cutter module 30, a transport module 32, and a piercing module 34, each being respectively electrically coupled to battery 26. Each of cutter module 30, transport module 32, and piercing module 34 is electrically and controllably coupled to controller circuit 18 by one or more electrical conductors, e.g., wires or circuit traces.

Cutter module 30 may include an electrical motor 30-1 having a shaft to which a cutter drive 30-2 is drivably connected. Transport module 32 may include an electrical motor 32-1 having a shaft to which a transport drive 32-2 is drivably connected. Piercing module 34 may include an electrical motor 34-1 having a shaft to which a piercing shot drive 34-2 is drivably connected. Each electrical motor 30-1, 32-1, 34-1 may be, for example, a direct current (DC) motor or stepper motor. Each of cutter drive 30-2, transport drive 32-2, and piercing shot drive 34-2 may include one or more of a gear, gear train, or belt/pulley arrangement.

Vacuum source 22 is electrically and controllably coupled to battery 26 by one or more electrical conductors, e.g., wires or circuit traces. Vacuum source 22 may include, for example, an electric motor 22-1 that drives a vacuum pump 22-2. Vacuum source 22 has a vacuum source port 22-3 coupled to vacuum pump 22-2 for establishing vacuum in biopsy probe assembly 14. Electric motor 22-1 may be, for example, a rotary, linear or vibratory DC motor. Vacuum pump 22-2 may be, for example, a peristaltic pump or a diaphragm pump, or one or more of each connected in series or parallel.

Vacuum sensor 24 is electrically coupled to controller circuit 18 by one or more electrical conductors, e.g., wires or circuit traces. Vacuum sensor 24 may be a pressure differential sensor that provides vacuum (negative pressure) feedback signals to controller circuit 18. In some implementations, vacuum sensor 24 may be incorporated into vacuum source 22.

Referring again to FIG. 1, biopsy probe assembly 14 is configured for releasable attachment to driver assembly 12. As used herein, the term "releasable attachment" means a configuration that facilitates an intended temporary connection followed by selective detachment involving a manipulation of disposable biopsy probe assembly 14 relative to driver assembly 12, without the need for tools.

Figure 3A:
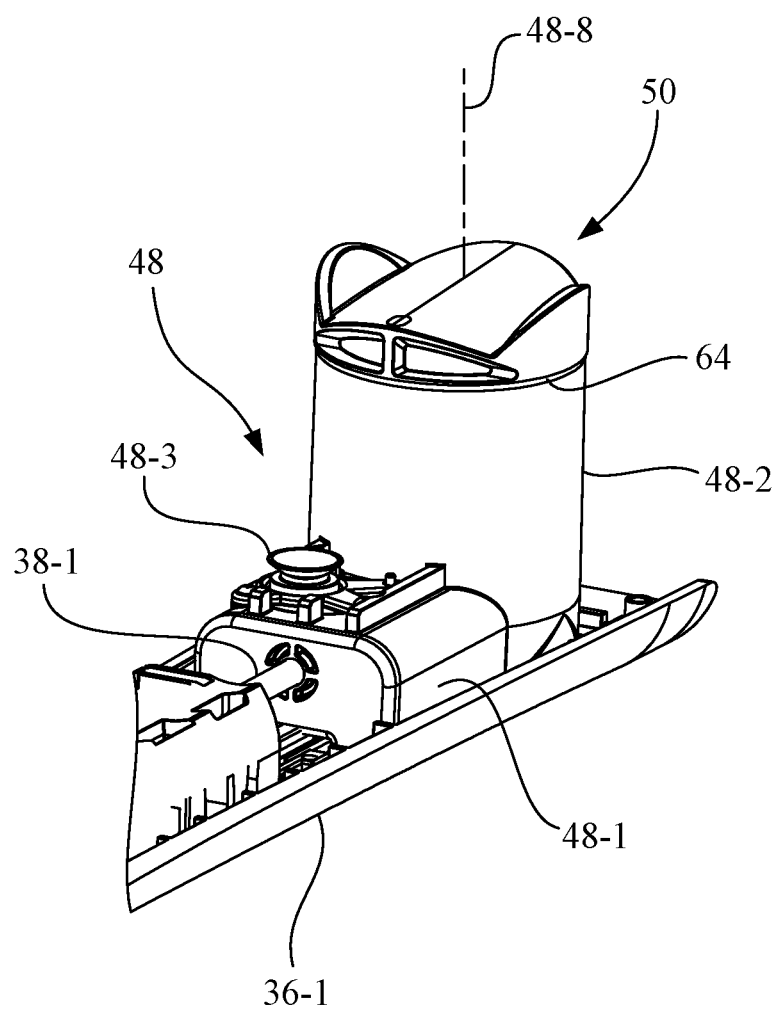
FIG. 3A is perspective view of a portion of the biopsy probe assembly of FIG. 1 that includes the sample manifold and a sample container in accordance with an aspect of the present invention.

Referring to FIGS. 1 and 3A, biopsy probe assembly 14 includes a probe housing 36, a vacuum cannula 38, a stylet cannula 40, a cutter cannula 42, a sample manifold 48, and a sample container 50. The portion of vacuum cannula 38, stylet cannula 40, cutter cannula 42 that extends distally on longitudinal axis 44 from front plate 36-2 of biopsy probe assembly 14 of biopsy apparatus 10 is referred to herein as a biopsy needle 52.

Probe housing 36 is formed as an L-shaped structure having an elongate portion 36-1 and a front plate 36-2. When biopsy probe assembly 14 is attached to driver assembly 12, front plate 36-2 is positioned distally adjacent to an entirety of front surface 16-1 of driver housing 16, i.e., so as to shield the entirety of front surface 16-1 of the non-disposable driver assembly from contact with a patient.

Vacuum cannula 38, stylet cannula 40, and cutter cannula 42 are coaxially arranged along a longitudinal axis 44 in a nested tube arrangement, with vacuum cannula 38 being the innermost tube, cutter cannula 42 being the outermost tube, and stylet cannula 40 being the intermediate tube that is interposed between vacuum cannula 38 and cutter cannula 42. In other words, vacuum cannula 38 is positioned inside stylet cannula 40, and stylet cannula 40 is positioned inside cutter cannula 42.

Vacuum cannula 38 is coupled in fluid communication with vacuum source 22 via sample manifold 48.

Stylet cannula 40 includes a sample notch 40-1 and a piercing tip 40-2. Sample notch 40-1 is formed as an elongate opening in stylet cannula 40 to facilitate a reception of tissue into a lumen of stylet cannula 40. Cutter cannula 42 has a distal cutting end 42-1.

Stylet cannula 40 and cutter cannula 42 are jointly connected to piercing shot drive 34-2. Upon a first actuation of prime/pierce button 28-2, stylet cannula 40 and cutter cannula 42 are translated in unison in proximal direction 46-1 along longitudinal axis 44 to position piercing shot drive 34-2, stylet cannula 40, and cutter cannula 42 in a ready, i.e., cocked position. A second actuation of prime/pierce button 28-2 effects a piercing shot, wherein piercing shot drive 34-2 is released from the cocked position, and in turn rapidly propels stylet cannula 40 and cutter cannula 42 in distal direction 46-2 along longitudinal axis 44 toward a distal-most position of the combined elements, e.g., within the patient.

Cutter cannula 42 is connected to cutter drive 30-2, and is individually retracted or extended along longitudinal axis 44 by activation of cutter module 30 of biopsy probe assembly 14 by activation of sample button 28-1 of user interface 28 to initiate a sample sequence. For example, cutter cannula 42 may be translated and retracted axially along longitudinal axis 44 to expose sample notch 40-1 during a sample sequence so that tissue may be pulled by vacuum into the lumen of stylet cannula 40 by vacuum provided by vacuum cannula 38. Thereafter, cutter cannula 42 may have a rotational cutting motion and may be translated axially along longitudinal axis 44 to extend over sample notch 40-1 such that distal cutting end 42-1 of cutter cannula 42 severs the tissue that is pulled by vacuum into the lumen of stylet cannula 40 by vacuum provided by vacuum cannula 38.

Stylet cannula 40 is individually retracted or extended along longitudinal axis 44 by activation of transport module 32 of biopsy probe assembly 14, so as to aid in delivery of a tissue sample into the lumen of vacuum cannula 38. Vacuum cannula 38 then transports the tissue sample, via vacuum, to sample manifold 48 by the vacuum supplied to sample manifold 48 by vacuum source 22.

Figure 3B:
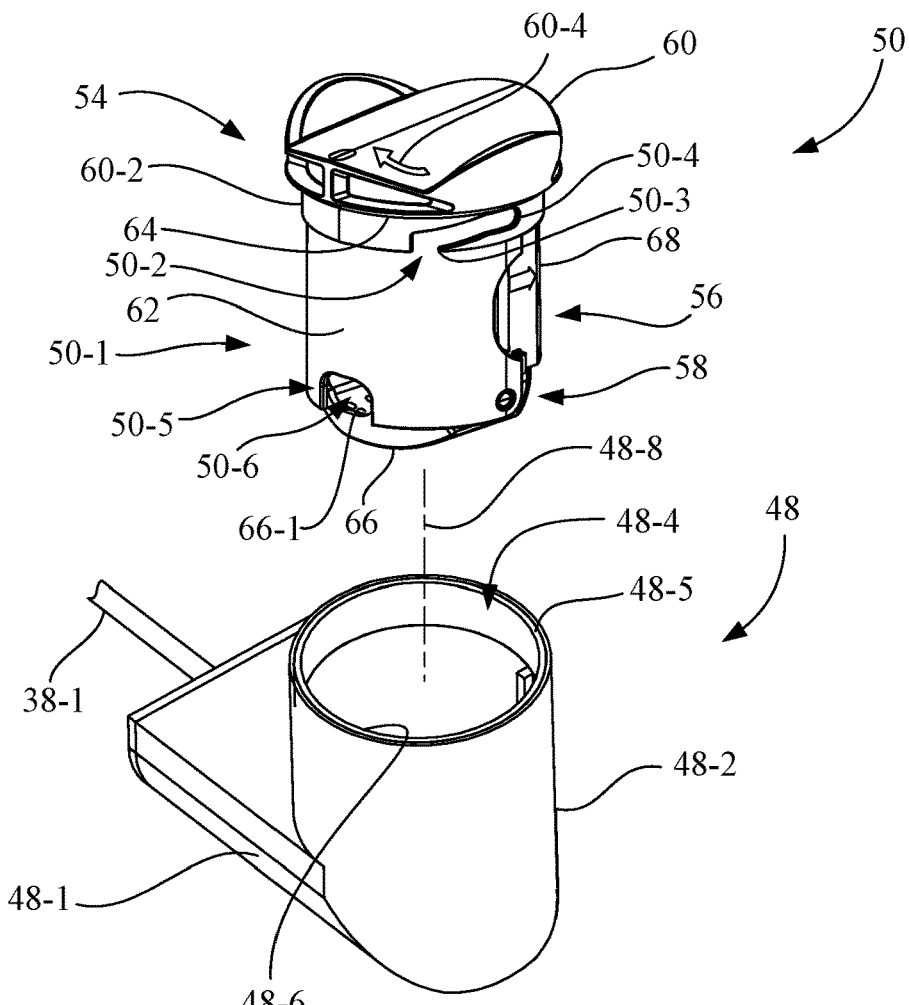
FIG. 3B is an exploded perspective view of a portion of the biopsy probe assembly of FIG. 1 that includes the sample manifold and sample container, with the sample container in an insertion orientation relative to the sample manifold.
Figure 3C:
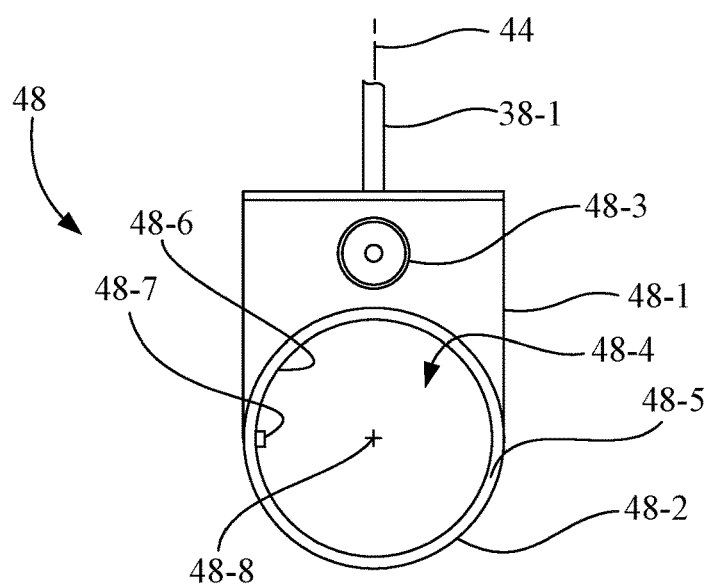
FIG. 3C is a top view of the sample manifold of FIGS. 3A and 3B.

Referring to FIGS. 3A-3C, sample manifold 48 is configured as an L-shaped structure having a vacuum chamber portion 48-1 and a collection chamber portion 48-2. Vacuum chamber portion 48-1 includes a vacuum input port 48-3 that is arranged to sealably engage vacuum source port 22-3 (see FIG. 2) of vacuum source 22 of driver assembly 12 when biopsy probe assembly 14 is attached to driver assembly 12. Blotting papers may be placed in vacuum chamber portion 48-1 in a region between vacuum input port 48-3 and collection chamber portion 48-2.

Vacuum chamber portion 48-1 is connected in fluid communication with collection chamber portion 48-2. A proximal end portion 38-1 of vacuum cannula 38 passes into vacuum chamber portion 48-1 and is in fluid communication with collection chamber portion 48-2.

Referring to FIGS. 3B and 3C, collection chamber portion 48-2 of sample manifold 48 defines a receptacle 48-4 that is sized and arranged to removably receive, and mount, sample container 50. Referring also to FIGS. 1, 2, and 3A, when sample container 50 is mounted in receptacle 48-4 of collection chamber portion 48-2 of sample manifold 48, sample container 50 is interposed between vacuum source 22 and proximal end portion 38-1 of vacuum cannula 38, such that sample container 50 is in direct fluid communication with proximal end portion 38-1 of vacuum cannula 38, and sample container 50 also is in direct fluid communication with vacuum input port 48-3 of vacuum chamber portion 48-1.

Thus, vacuum generated by vacuum source 22 is delivered to proximal end portion 38-1 of vacuum cannula 38 via sample manifold 48 and sample container 50. Accordingly, when vacuum is applied by vacuum source 22 at vacuum input port 48-3 of vacuum chamber portion 48-1 of sample manifold 48, the vacuum passes through sample container 50, such that a tissue sample severed by cutter cannula 42 at sample notch 40-1 of stylet cannula 40 may be transported by vacuum, through vacuum cannula 38, and into sample container 50.

Referring to FIGS. 3B and 3C, receptacle 48-4 of collection chamber portion 48-2 of sample manifold 48 has an open end 48-5, an interior side wall 48-6, and a mounting pin 48-7. Collection chamber portion 48-2 has an insertion axis 48-8. Mounting pin 48-7 is formed on interior side wall 48-6 of receptacle 48-4 and projects inwardly from the interior side wall 48-6 toward insertion axis 48-8.

In the present embodiment, sample container 50 is configured so as to mate with receptacle 48-4 of collection chamber portion 48-2 of sample manifold 48 in such a way that sample container 50 can only be loaded into receptacle 48-4 in one orientation and in one direction, thereby reducing operator errors after removal and reloading sample container 50 to take additional tissue samples.

Referring also to FIGS. 4A-4E, sample container 50 has a cap portion 54 and a basket portion 56, which are joined by a hinge 58, and which when in a closed position, fit together to define a cylindrical side wall 50-1. Each of cap portion 54 and a basket portion 56 may be made of a rigid plastic, and may have smooth surface features to reduce radiograph visibility impact if tissue sample radiographs are desired, or required. The rigid plastic may also be selected for compatibility with formalin.

Referring also to FIGS. 3B and 3C, sample container 50 is sized and configured to be removably received in receptacle 48-4 of collection chamber portion 48-2 of sample manifold 48. For example, sample container 50 and interior side wall 48-6 of receptacle 48-4 may have complementary cylindrical shapes and are axially aligned along an insertion axis 48-8. Cylindrical side wall 50-1 of sample container 50 has an outside diameter that is selected to be slidably received by cylindrical interior side wall 48-6 of receptacle 48-4. As used herein, the term "cylindrical" means a generally arcuate-shaped annular contour that may include flats, ledges, and/or other surface features not associated with a pure cylinder.

Referring to FIGS. 4A-4E, sample container 50 includes a mounting channel 50-2 that is sized and positioned to engage and follow mounting pin 48-7 of receptacle 48-4 of sample manifold 48 (see FIG. 3C). Mounting channel 50-2 spirals an arcuate distance of less than one turn of sample container 50, e.g., one-eighth turn to one-quarter of the circumference of sample container 50 (depending on design parameters), downwardly from cap portion 54 along cylindrical side wall 50-1. Mounting channel 50-2 has an open end 50-3 and a closed end 50-4. Open end 50-3 is positioned to receive mounting pin 48-7 of receptacle 48-4 of collection chamber portion 48-2 of sample manifold 48 and to provide an initial indexing (rotational orientation) of sample container 50 relative to receptacle 48-4 of collection chamber portion 48-2 of sample manifold 48 about insertion axis 48-8.

When mounting pin 48-7 of receptacle 48-4 of collection chamber portion 48-2 of sample manifold 48 is received in open end 50-3 of mounting channel 50-2 of sample container 50, a rotation (clockwise in the present example) of sample container 50 causes mounting pin 48-7 to follow the spiral shape of mounting channel 50-2 toward closed end 50-4 as sample container 50 is rotated, so as to pull sample container 50 along insertion axis 48-8 into receptacle 48-4 of collection chamber portion 48-2 of sample manifold 48.

It is contemplated that mounting channel 50-2 could include multiple spiral channels formed in sample container 50, if desired. In this case, receptacle 48-4 of collection chamber portion 48-2 of sample manifold 48 may have a number of mounting pins that correspond to the number of spiral channels formed in sample container 50, each of which being received in a respective spiral channel of sample container 50 as sample container 50 is received in receptacle 48-4 of collection chamber portion 48-2 of sample manifold 48.

Referring to FIGS. 4A-4E, cap portion 54 of sample container 50 includes a lid 60 and a partial side wall 62 that may be formed as a one-piece unitary structure. Lid 60 includes a domed cap 60-1, an annular rim 60-2, and an annular lip 60-3. Annular rim 60-2 joins domed cap 60-1 to define annular lip 60-3. Mounting channel 50-2 is formed in, and spirals around, annular rim 60-2. Domed cap 60-1 may include an arrow indicia 60-4, e.g., raised or embossed, to indicate a rotation direction for effecting the mounting of sample container 50 in receptacle 48-4 of collection chamber portion 48-2 of sample manifold 48.

A seal 64, such as an O-ring, may be placed around annular rim 60-2, such that when sample container 50 is mounted in receptacle 48-4 of collection chamber portion 48-2 of sample manifold 48, seal 64 provides a vacuum-tight seal between sample container 50 and receptacle 48-4 of collection chamber portion 48-2 of sample manifold 48. Advantageously, a reverse rotation of sample container 50 causes mounting channel 50-2 to follow the spiral shape of mounting pin 48-7 toward open end 50-3, so as to pull sample container 50 along insertion axis 48-8 out of receptacle 48-4 to aid in releasing the vacuum seal.

In one embodiment, at least the domed cap 60-1 of cap portion 54 is transparent, or translucent, so as to permit visual inspection of the contents of sample container 50 without having to remove sample container 50 from receptacle 48-4 of collection chamber portion 48-2 of sample manifold 48. By rounding domed cap 60-1 of cap portion 54, the interior of sample container 50 may be observed from multiple angles while holding biopsy apparatus 10 or observing the biopsy procedure. Also, domed cap 60-1 of cap portion 54 may include a magnification feature to further improve visibility of the contents of sample container 50, e.g., during a biopsy.

Figure 4A:
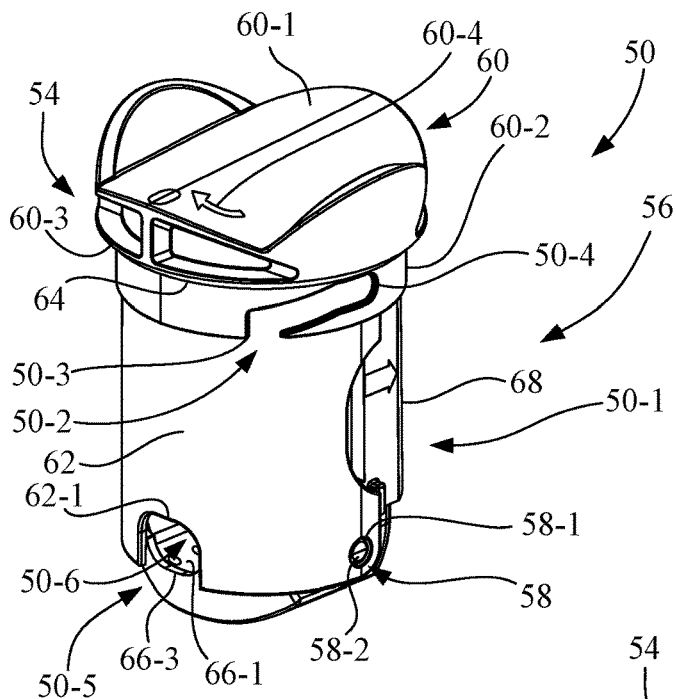
FIG. 4A is perspective view of the sample container of FIGS. 3A and 3B, with the sample container in the closed position.
Figure 4B:
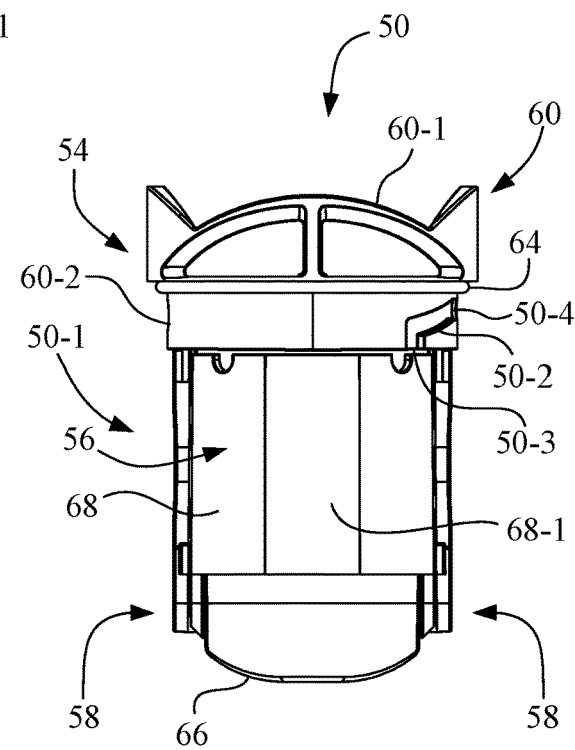
FIG. 4B is an end view of the sample container of FIGS. 3A and 3B, with the sample container in the closed position.
Figure 4C:
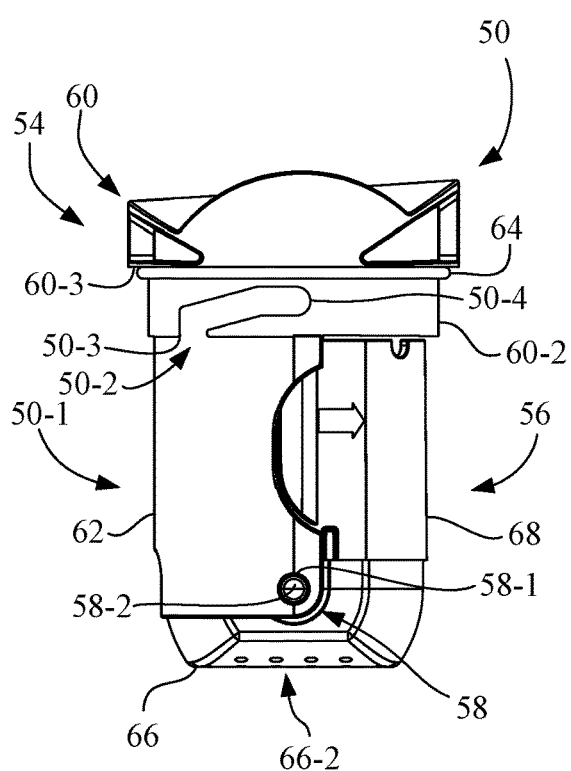
FIG. 4C is a side view of the sample container of FIGS. 3A and 3B, with the sample container in the closed position.
Figure 4D:
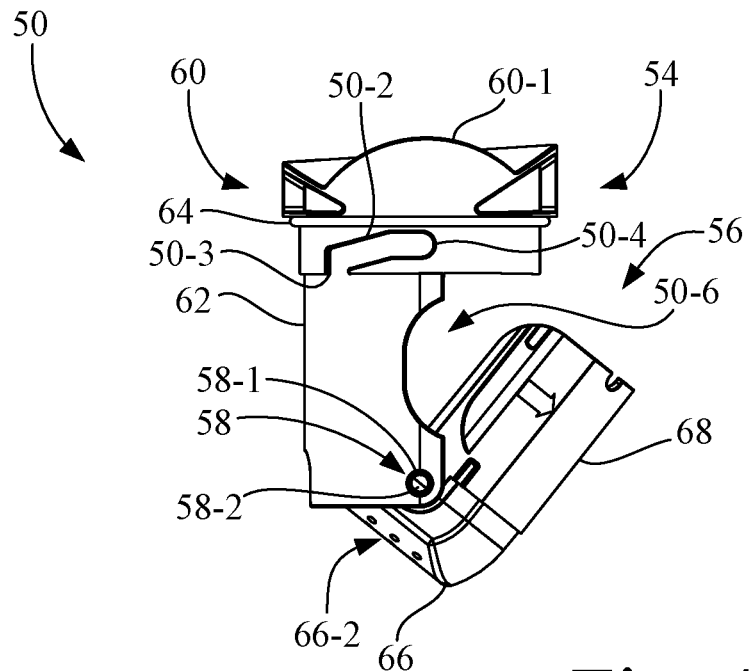
FIG. 4D is a side view of the sample container of FIGS. 3A and 3B, with the sample container in an intermediate open position.
Figure 4E:
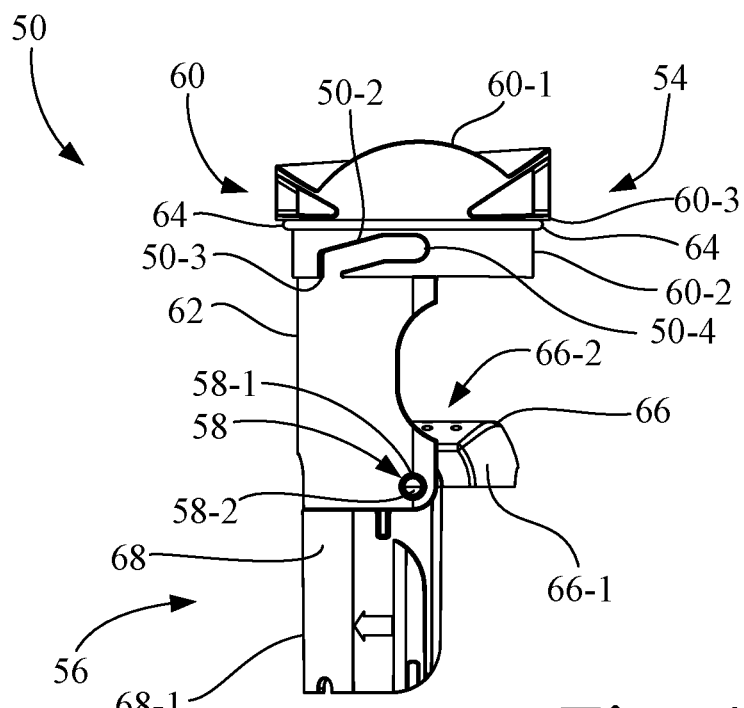
FIG. 4E is a side view of the sample container of FIGS. 3A and 3B, with the sample container in a fully open position.

Referring to FIGS. 4C-4E, basket portion 56 includes a floor 66 and a partial side wall 68 that may be formed as a one-piece unitary structure. Partial side wall 68 extends upwardly from floor 66. In the present embodiment, floor 66 has a concave interior surface 66-1 and includes a plurality of holes 66-2 (see also FIG. 4A). The plurality of holes 66-2 in floor 66 of sample container 50 allow vacuum to travel through sample container 50 during a biopsy procedure, and the tissue specimens will be delivered from biopsy needle 52 onto concave interior surface 66-1 of floor 66 of sample container 50. In addition, following the biopsy procedure, sample container 50 may be placed directly into a specimen jar containing formalin, wherein the plurality of holes 66-2 in floor 66 of sample container 50 allow for formalin to infuse into sample container 50.

Referring to FIGS. 4A-4E, cap portion 54 and a basket portion 56 are joined by hinge 58 located at a bottom portion of sample container 50. Hinge 58 has engageable hinge features formed on both of cap portion 54 and a basket portion 56. In the present embodiment, for example, hinge 58 includes a pair of opposed apertures 58-1 formed in a lower distal portion of partial side wall 62 of cap portion 54 and a corresponding pair of opposed pins 58-2 that extend radially outwardly from partial side wall 68 of basket portion 56 just above floor 66, wherein the pair of opposed pins 58-2 are received in the pair of opposed apertures 58-1, e.g., holes, to form a pivot joint. This pivot joint provides ease of access to the tissue specimens contained in sample container 50. The hinge action of cap portion 54 and basket portion 56 also may create a scooping action to aid in specimen retrieval as sample container 50 is opened.

It is also contemplated that the engageable hinge features of the pin/hole arrangement can be reversed, if desired, such that the pins are on partial side wall 62 of cap portion 54 and the holes are in partial side wall 68 of the basket portion 56.

As an alternative to forming apertures 58-1 as holes, it is contemplated that apertures 58-1 may be formed as slots or channels, such that the pair of opposed pins 58-2 of hinge 58 may be readily disengaged from apertures 58-1 when sample container 50 is opened, so as to facilitate easy removal of basket portion 56 from cap portion 54 after basket portion 56 has been opened to a predefined position relative to cap portion 54, if desired.

FIGS. 4A-4C depict sample container 50 in a closed position, with partial side wall 62 of cap portion 54 overlapping partial side wall 68 of basket portion 56 to form a snap fit. Advantageously, by joining cap portion 54 and basket portion 56 with hinge 58, an operator must take a deliberate action to open sample container 50 to remove the tissue samples, and there is no risk of accidentally detaching a lid or piece of the container when removing it from biopsy apparatus 10. The tissue samples (specimens) are retained in sample container 50 until opened, reducing the risk of tissue sample loss during transport.

Sample container 50 must be in the closed position depicted in FIGS. 4A-4C in order for sample container 50 to be receivable into receptacle 48-4 of collection chamber portion 48-2 of sample manifold 48 (see also FIGS. 3B and 3C) so that sample container 50 can be seated in and mounted to sample manifold 48 (see also FIG. 3A). As shown in FIGS. 3B and 4A, when sample container 50 is in the closed position, cap portion 54 and basket portion 56 together define an aperture 50-5 and an interior sample chamber 50-6. Proximal end portion 38-1 of vacuum cannula 38 extends to aperture 50-5 to deliver, via vacuum, tissue samples from biopsy needle 52 into interior sample chamber 50-6 and onto concave interior surface 66-1 of floor 66 having the plurality of holes 66-2 (see also FIG. 4C). In the present embodiment, aperture 50-5 of sample container 50 is formed by locating a semicircular aperture 62-1 in partial side wall 62 of cap portion 54 adjacent to a semicircular aperture 66-3 located above floor 66 of basket portion 56, when sample container 50 is in the closed position.

FIGS. 4D and 4E show a sequence of opening sample container 50, wherein one or both of cap portion 54 and basket portion 56 are pivoted around hinge 58 such that the contents of sample container 50 may be accessed. FIG. 4D shows sample container 50 at an intermediate open position, and FIG. 4E shows sample container 50 is a completely open position. When sample container 50 is placed in the completely open position and oriented on its side, a flat exterior feature 68-1 on partial side wall 68 of basket portion 56 allows sample container 50 to rest on a flat surface, such as a table top or procedure tray, thereby reducing the risk of sample container 50 rolling off the flat surface.

Referring to FIG. 5, with reference to FIG. 1, in some procedures an operator may desire to use a coaxial introducer cannula 70 to maintain an access path to the biopsy site, e.g., to the lesion, such that biopsy needle 52 of biopsy apparatus 10 may be removed from the biopsy site, while maintaining the ability to reinsert biopsy needle 52, or to insert another medical apparatus, such as a tissue marker deploying device, at the biopsy site.

Referring also to FIGS. 6A-6C, coaxial introducer cannula 70 includes a coaxial cannula 72 and a hub 74. Coaxial cannula 72 may be formed as an elongate tube, e.g., a metal tube such as a stainless steel tube, having a proximal portion 72-1 and a distal end 72-2. Hub 74 is made from a rigid plastic which is fixedly attached (e.g., overmolded, adhesively connected, etc.) to a proximal portion 72-1 of coaxial cannula 72.

Coaxial cannula 72 of coaxial introducer cannula 70 is sized to be coaxially and slidably received along longitudinal axis 44 over biopsy needle 52 formed by stylet cannula 40 and cutter cannula 42. Hub 74 of coaxial introducer cannula 70 is configured for releasable attachment to front plate 36-2 of probe housing 36 of biopsy apparatus 10.

In the present embodiment, referring also to FIG. 5, front plate 36-2 of probe housing 36 includes a catch 76 formed as a set of slotted protrusions 78-1, 78-2 that protrude outwardly from front plate 36-2 of probe housing 36 of biopsy apparatus 10. Slotted protrusions 78-1, 78-2 have respective opposed slots 80-1, 80-2 which face in a direction toward longitudinal axis 44.

Referring to FIGS. 5 and 6A-6C, in the present embodiment hub 74 includes a hub body 82, latching lever 84, and a latch 86. Latching lever 84 is an elongate arm that extends radially from hub body 82 relative to longitudinal axis 44. Latch 86 is configured to rotatably engage catch 76 of front plate 36-2 of biopsy probe assembly 14 of biopsy apparatus 10. In the present embodiment, latch 86 is in the form of a set of tabs 86-1, 86-2 that extends radially outwardly from hub body 82.

As shown in FIG. 5, latching lever 84 is longer than a height of front plate 36-2 of probe housing 36 and driver assembly 12, so that latching lever 84 can be reached and rotationally operated by the operator's thumb or finger while the operator grasps biopsy apparatus 10 with the same hand, thereby facilitating single-handed rotation of the coaxial introducer cannula relative to front plate 36-2 of biopsy probe assembly 14 of biopsy apparatus 10, so as to effect a respective engagement and disengagement of catch 76 of coaxial introducer cannula 70 and latch 86 of front plate 36-2 of biopsy probe assembly 14 of biopsy apparatus 10.

Also, optionally, referring to FIGS. 5, 6A and 6B, a first lock feature 88-1 may be provided at front plate 36-2 of probe housing 36 and a second lock feature 88-2 may be provided on hub 74 of coaxial introducer cannula 70, which when engaged, resists rotation of coaxial introducer cannula 70 about longitudinal axis 44, i.e., relative to biopsy apparatus 10. More particularly, second lock feature 88-2 may be positioned on or in latching lever 84.

Referring to FIGS. 5 and 6A-6C, during installation of coaxial introducer cannula 70 on biopsy apparatus 10, coaxial cannula 72 of coaxial introducer cannula 70 is coaxially and slidably received along longitudinal axis 44 over biopsy needle 52 formed by stylet cannula 40 and cutter cannula 42. With the set of tabs 86-1, 86-2 of hub 74 of coaxial introducer cannula 70 rotationally misaligned from slotted protrusions 78-1, 78-2 of front plate 36-2 of probe housing 36 shown in FIG. 5, coaxial introducer cannula 70 is moved axially along longitudinal axis 44 until hub 74 is axially seated against front plate 36-2 of probe housing 36. As shown in FIG. 6C, latching lever 84 is angled proximally relative to hub body 82, such that latching lever 84 engages front plate 36-2 shown in FIG. 5 prior to being axially seated against front plate 36-2, and latching lever 84 is deflected, as a cantilever spring, in distal direction 46-2.

Latching lever 84 of hub 74 is then rotated about longitudinal axis 44 to a latched position, depicted in FIG. 5, wherein latch 86, e.g., the set of tabs 86-1, 86-2, of hub 74 is received in the catch 76, e.g., the opposed slots 80-1, 80-2 of the set of slotted protrusions 78-1, 78-2, of front plate 36-2 of probe housing 36, so as to connect coaxial introducer cannula 70 to biopsy apparatus 10 to thereby prevent axial movement of coaxial introducer cannula 70 relative to biopsy apparatus 10 along longitudinal axis 44. The rotational motion of latching lever 84 may be either clockwise or counterclockwise to allow for ambidextrous operation. First lock feature 88-1 of front plate 36-2 of probe housing 36 is now also engaged with the second lock feature 88-2 on latching lever 84 of hub 74 of coaxial introducer cannula 70, so as to resist rotation of coaxial introducer cannula 70 about longitudinal axis 44.

In the present embodiment, first lock feature 88-1 of front plate 36-2 of probe housing 36 and second lock feature 88-2 of hub 74 of coaxial introducer cannula 70 are complementary engagement features, such as a hole/protrusion arrangement or a magnetic arrangement, which when engaged will resist, but not prohibit, rotation of coaxial introducer cannula 70 about longitudinal axis 44. For example, second lock feature 88-2 may be a notch or opening formed in the proximal surface of latching lever 84 of hub 74, and first lock feature 88-1 of front plate 36-2 of probe housing 36 may be a raised distally facing area, e.g., a pin and/or headlamp, on front plate 36-2 that mates with the notch formed in latching lever 84, or vice-versa, or both, so as to provide resistance to a rotation of coaxial introducer cannula 70 about longitudinal axis 44, i.e., relative to biopsy apparatus 10.

In order to disconnect coaxial introducer cannula 70 from biopsy apparatus 10, latching lever 84 is rotated about longitudinal axis 44 to disengage latch 86, e.g., the set of tabs 86-1, 86-2, of hub 74 of coaxial introducer cannula 70 from catch 76, e.g., the opposed slots 80-1, 80-2 of the set of slotted protrusions 78-1, 78-2, of front plate 36-2 of probe housing 36. The rotational motion of latching lever 84 may be either clockwise or counterclockwise to allow for ambidextrous operation. Coaxial introducer cannula 70 is now free to move axially along longitudinal axis 44 in distal direction 46-2 away from front plate 36-2 of probe housing 36 to remove coaxial introducer cannula 70 from biopsy needle 52 of biopsy apparatus 10. Since latching lever 84 is resilient, as latching lever 84 returns to its pre-deflection position, and the cantilever spring action generated by latching lever 84 pushes against front plate 36-2 so as to aid in moving coaxial introducer cannula 70 in distal direction 46-2 away from its seated position.

Alternatively, in one magnet configuration for first lock feature 88-1 and second lock feature 88-2, for example, front plate 36-2 of probe housing 36 may have a center magnet having a polarity to attract a magnet embedded in, or attached to, latching lever 84 of hub 74 when coaxial introducer cannula 70 is in the latched position, so as to resist rotation of coaxial introducer cannula 70 relative to biopsy apparatus 10. Front plate 36-2 of probe housing 36 also may have two rotationally spaced magnets, one on either side of the center magnet, having a polarity the same as that of the hub magnet, so as to repel the hub magnet in distal direction 46-2 to assist the operator in axial removal of coaxial introducer cannula 70 from biopsy probe assembly 14 of biopsy apparatus 10 after latching lever 84 has been rotated to disconnect coaxial introducer cannula 70 from biopsy apparatus 10.

It is contemplated that coaxial introducer cannula 70 may be used with, and connected to, other types of biopsy apparatus, such as a trocar adapted to include catch 76, e.g., the slotted protrusions 78-1, 78-2, and to optionally include first lock feature 88-1.

FIGS. 7A, 7B, 8A, and 8B are directed to another embodiment for connection of a coaxial introducer cannula in accordance with the present invention, with probe housing 36.

FIGS. 7A, 7B, 8A, and 8B are directed to another embodiment for connection of a coaxial introducer cannula with probe housing 36 of biopsy apparatus 10.

Figure 8A:
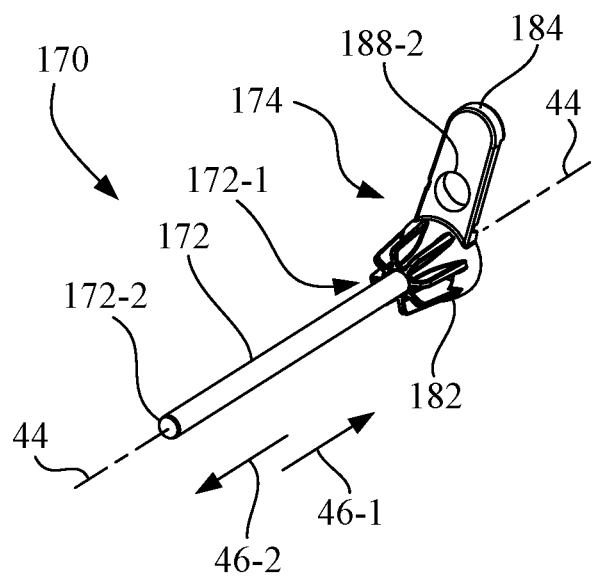
FIG. 8A is a perspective view of an alternative coaxial introducer cannula configured for connection to the alternative connection configuration of the probe housing of FIGS. 7A and 7B.
Figure 8B:
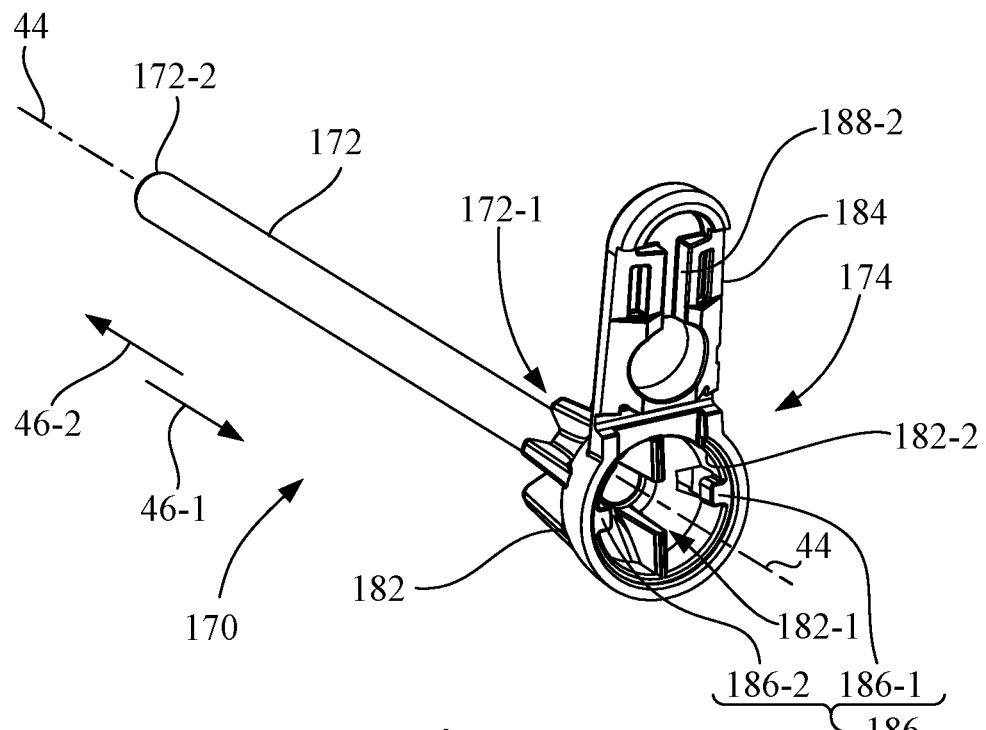
FIG. 8B is a rear perspective view of the alternative coaxial introducer cannula of FIG. 8A.

Referring to FIGS. 8A and 8B, in the present embodiment, a coaxial introducer cannula 170 includes a coaxial cannula 172 and a hub 174. Coaxial cannula 172 may be formed as an elongate tube, e.g., a metal tube such as a stainless steel tube, having a proximal portion 172-1 and a distal end 172-2. Hub 174 is made from a rigid plastic which is fixedly attached (e.g., overmolded, adhesively connected, etc.) to a proximal portion 172-1 of coaxial cannula 172.

Coaxial cannula 172 of coaxial introducer cannula 170 is sized to be coaxially and slidably received along longitudinal axis 44 over biopsy needle 52 formed by stylet cannula 40 and cutter cannula 42 (see also FIG. 1). Hub 174 of coaxial introducer cannula 170 is configured for releasable attachment to front plate 36-2 of probe housing 36 of biopsy apparatus 10 (see FIGS. 7A and 7B).

Figure 7A:
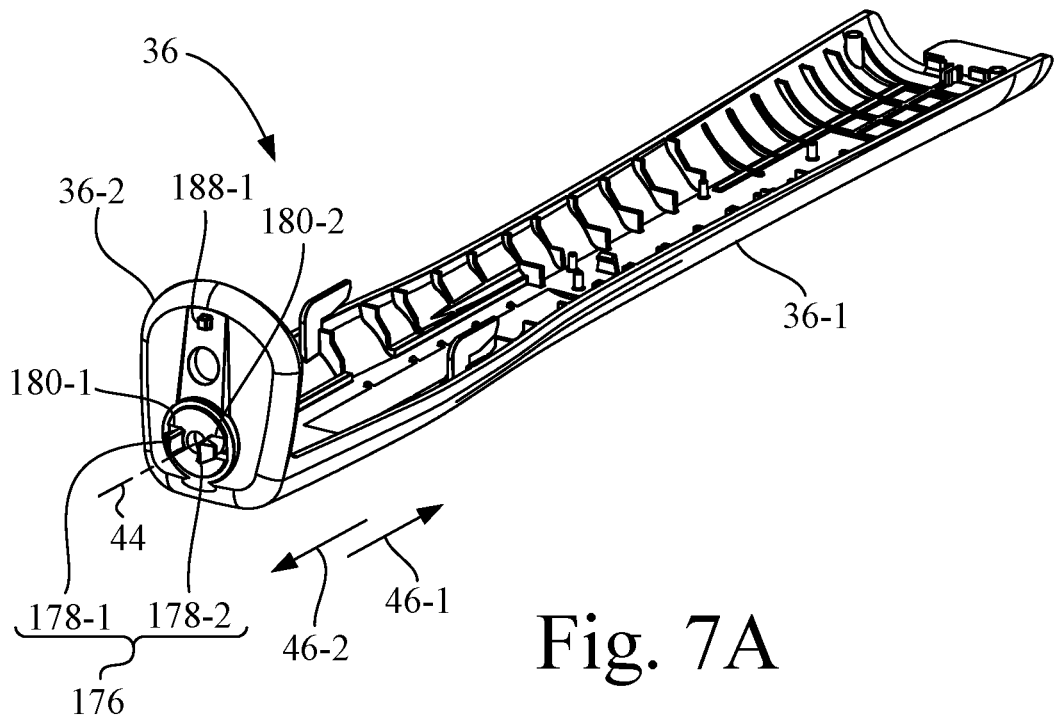
FIG. 7A is a perspective view of the probe housing of the biopsy apparatus of FIG. 1, with an alternative configuration for connection to a coaxial introducer cannula.
Figure 7B:
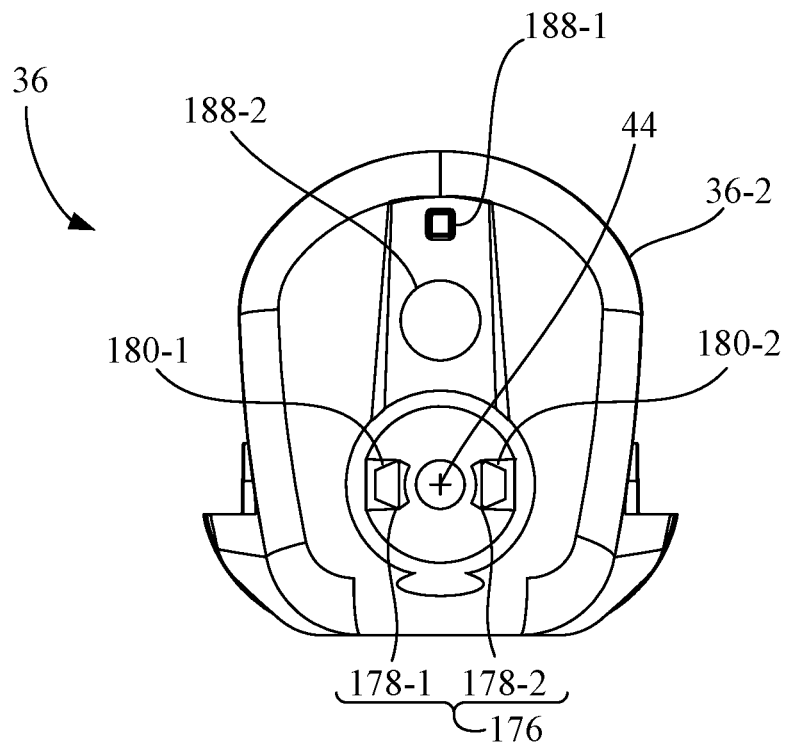
FIG. 7B is an end view of the probe housing of FIG. 7A.

As shown in FIGS. 7A and 7B, in the present embodiment, front plate 36-2 of probe housing 36 includes a catch 176 formed as a set of slotted protrusions 178-1, 178-2 that protrude outwardly in distal direction 46-2 from front plate 36-2 of probe housing 36 of biopsy apparatus 10. Slotted protrusions 178-1, 178-2 have respective opposed slots 180-1, 180-2 which face in a direction away from longitudinal axis 44.

As shown in FIGS. 8A and 8B, in the present embodiment, hub 174 includes a hub body 182, latching lever 184, and a latch 186. Latch 186 is configured to rotatably engage catch 176 of front plate 36-2 of biopsy probe assembly 14 of biopsy apparatus 10. Latching lever 184 is an elongate arm that extends radially from hub body 182 relative to longitudinal axis 44. As shown in FIG. 8B, hub body 182 has a cylindrical recess 182-1 defining a side wall 182-2. Latch 186 is in the form of a set of tabs 186-1, 186-2 that extend radially inwardly from side wall 182-2 of cylindrical recess 182-1 of hub body 182, toward longitudinal axis 44.

Latching lever 184 is longer than a height of front plate 36-2 of probe housing 36 and driver assembly 12 (see FIG. 1), so that latching lever 184 can be reached and rotationally operated by the operator's thumb or finger while the operator grasps biopsy apparatus 10 with the same hand, thereby facilitating single-handed rotation of coaxial introducer cannula 170 relative to front plate 36-2 of biopsy probe assembly 14 of biopsy apparatus 10, so as to effect a respective engagement or disengagement of latch 186 of coaxial introducer cannula 170 with catch 176 of front plate 36-2 of biopsy probe assembly 14 of biopsy apparatus 10.

Also, optionally, a first lock feature 188-1 may be provided at front plate 36-2 of probe housing 36 and a second lock feature 188-2 may be provided on hub 174 of coaxial introducer cannula 170, which when engaged, resists rotation of coaxial introducer cannula 170 about longitudinal axis 44, i.e., relative to biopsy apparatus 10. More particularly, second lock feature 188-2 may be positioned on or in latching lever 184.

Referring to FIGS. 7A, 7B, 8A, and 8B (with reference to FIG. 1), during installation of coaxial introducer cannula 170 on biopsy apparatus 10, coaxial cannula 172 of coaxial introducer cannula 170 is coaxially and slidably received along longitudinal axis 44 over biopsy needle 52 formed by stylet cannula 40 and cutter cannula 42 (see FIG. 1). With the latch 186, e.g., the set of tabs 186-1, 186-2, of hub 174 of coaxial introducer cannula 170 rotationally misaligned from catch 176, e.g., the slotted protrusions 178-1, 178-2, of front plate 36-2 of probe housing 36, coaxial introducer cannula 170 is moved axially along longitudinal axis 44 until hub 174 and is axially seated against front plate 36-2 of probe housing 36. Latching lever 184 may be angled proximally relative to hub body 182, such that latching lever 184 engages front plate 36-2 prior to being axially seated against front plate 36-2 and latching lever 184 is deflected, as a cantilever spring, in distal direction 46-2.

Latching lever 184 of hub 174 is then rotated about longitudinal axis 44 to a latched position, wherein latch 186, e.g., the set of tabs 186-1, 186-2 of hub 174 are respectively received in catch 176, e.g., the opposed slots 180-1, 180-2 of the set of slotted protrusions 178-1, 178-2, of front plate 36-2 of probe housing 36, so as to connect coaxial introducer cannula 170 to probe housing 36, and thus to biopsy apparatus 10, to thereby prevent axial movement of coaxial introducer cannula 170 relative to biopsy apparatus 10 along longitudinal axis 44. The rotational motion of latching lever 184 may be either clockwise or counterclockwise to allow for ambidextrous operation. First lock feature 188-1 of front plate 36-2 of probe housing 36 is now also engaged with the second lock feature 188-2 on latching lever 184 of hub 174 of coaxial introducer cannula 170, so as to resist rotation of coaxial introducer cannula 170 about longitudinal axis 44.

In the present embodiment, first lock feature 188-1 of front plate 36-2 of probe housing 36 and second lock feature 188-2 of hub 174 of coaxial introducer cannula 170 are complementary engagement features, such as a slot/protrusion arrangement, which when engaged will resist, but not prohibit, rotation of coaxial introducer cannula 170 about longitudinal axis 44. For example, second lock feature 188-2 may be an opening, e.g., hole and/or slot, formed in a proximal surface of latching lever 184 of hub 174, and first lock feature 188-1 of front plate 36-2 of probe housing 36 may be a raised distally facing area, e.g., a pin and/or headlamp, on front plate 36-2 that mates with the opening formed in latching lever 184, or vice-versa, or both, so as to provide resistance to a rotation of coaxial introducer cannula 170 about longitudinal axis 44, i.e., relative to biopsy apparatus 10.

In order to disconnect coaxial introducer cannula 170 from biopsy apparatus 10, latching lever 184 is rotated about longitudinal axis 44 to disengage latch 186, e.g., the set of tabs 186-1, 186-2, of hub 174 of coaxial introducer cannula 170 from catch 176, e.g., the opposed slots 180-1, 180-2 of the set of slotted protrusions 178-1, 178-2, of front plate 36-2 of probe housing 36. The rotational motion of latching lever 184 may be either clockwise or counterclockwise to allow for ambidextrous operation. Coaxial introducer cannula 170 is now free to move axially along longitudinal axis 44 in distal direction 46-2 away from front plate 36-2 of probe housing 36 to remove coaxial introducer cannula 170 from biopsy needle 52 of biopsy apparatus 10.

Figure 9:
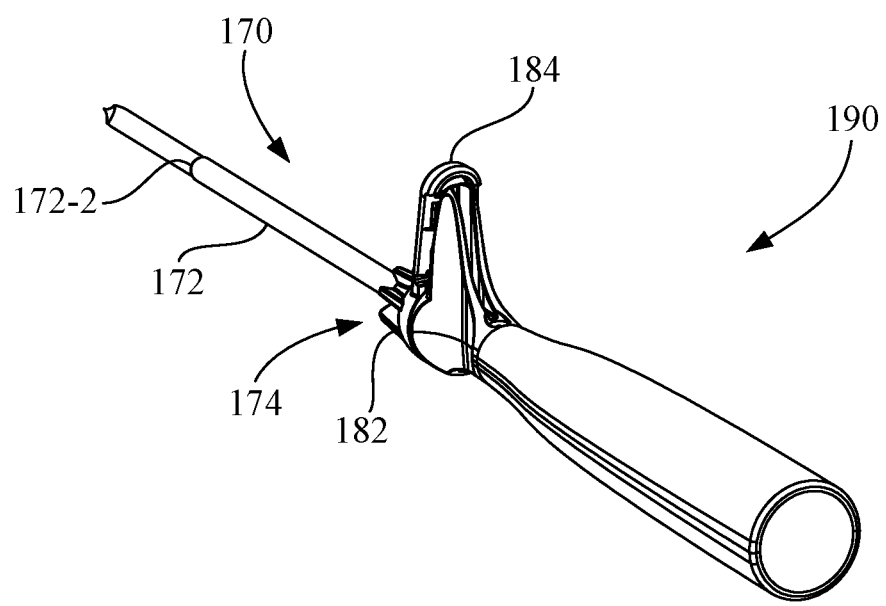
FIG. 9 is perspective view of a trocar configured for use with the coaxial introducer cannula of FIGS. 8A and 8B.

Referring to FIG. 9, it is contemplated that coaxial introducer cannula 170 may be used with, and connected to, other types of biopsy apparatus, such as a trocar 190 adapted to include catch 176, e.g., the slotted protrusions 178-1, 178-2, and to optionally include first lock feature 188-1.

The following items also relate to the invention:

In one form, the invention relates to a biopsy apparatus, or alternatively to a biopsy probe assembly, that includes a biopsy needle, a sample manifold, and a sample container. The sample manifold is coupled to the biopsy needle. The sample manifold has a receptacle and an insertion axis. The sample receptacle has an interior side wall and a mounting pin that projects inwardly from the interior side wall toward the insertion axis. The sample container is configured for insertion into the receptacle. The sample container includes a mounting channel that is sized and positioned (structured) to engage and follow the mounting pin of the receptacle as the sample container is rotated.

Optionally, the mounting channel is configured to spiral an arcuate distance of less than one turn of the sample container.

Optionally, the mounting channel has an open end and a closed end. The open end is positioned to receive the mounting pin of the sample manifold to provide a rotational orientation of the sample container relative to the receptacle of the sample manifold about the insertion axis.

The biopsy apparatus may be configured such that, when the mounting pin of the receptacle is received in the open end of the mounting channel of the sample container, a rotation of the sample container causes the mounting pin to follow the spiral shape of the mounting channel toward the closed end, so as to pull the sample container along the insertion axis into the receptacle of the manifold.

The sample container may have a cap portion and a basket portion that are joined by a hinge to facilitate a pivot of one or both of the cap portion and the basket portion around the hinge between a closed position and an open position. The open position provides access to contents of the sample container.

The biopsy apparatus may be configured such that, when the sample container is in the closed position, a partial side wall of the cap portion overlaps a partial side wall of the basket portion to form a snap fit.

The cap portion of the sample container may include a lid and a partial side wall. The lid may include a domed cap and an annular rim. The annular rim may join the domed cap to define an annular lip. The mounting channel may be formed in, and spiral around, the annular rim.

The domed cap may be transparent or translucent to permit visual inspection of the contents of the sample container without having to remove the sample container from the receptacle of the manifold.

The domed cap may include a magnification feature.

A seal may be placed around the annular rim to provide a vacuum-tight seal between the sample container and the receptacle of the manifold.

The basket portion may include a floor having a concave interior surface and a plurality of holes. The biopsy apparatus may be configured such that the plurality of holes allows a vacuum to travel through the sample container to deliver a tissue sample from the biopsy needle onto the concave interior surface of the floor.

The cap portion and the basket portion of the sample container together may define an aperture and an interior sample chamber. The biopsy needle may include a vacuum cannula having a proximal end portion that extends to the aperture to deliver, via vacuum, tissue samples from the biopsy needle into the interior sample chamber.

The aperture of the sample container may be formed by a first semicircular aperture of the cap portion positioned adjacent a second semicircular aperture of the basket portion when the sample container is in a closed position.

Any of the features described herein may be combined in a biopsy apparatus, or alternatively in a biopsy probe assembly.

Optionally, a coaxial introducer cannula for use with the biopsy apparatus may be provided. The biopsy apparatus has a front plate having a catch, and a biopsy needle extends from the front plate on a longitudinal axis. The coaxial introducer cannula includes a coaxial cannula and a hub. The coaxial cannula is sized to be coaxially and slidably received over the biopsy needle. The hub is fixedly attached to a proximal portion of the coaxial cannula. The hub has a hub body, a latching lever, and a latch. The latch is configured to rotatably engage the catch. The latching lever extends radially from the hub body relative to the longitudinal axis. The latching lever is longer than a height of the front plate so that the latching lever can be reached and rotationally operated to rotate the hub relative to the front plate of the biopsy apparatus, thereby facilitating single-handed rotation of the coaxial introducer cannula relative to the front plate, so as to effect a respective engagement or disengagement of the latch of the coaxial introducer cannula with the catch of the front plate.

A rotational motion of the latching lever may be either clockwise or counterclockwise to allow for ambidextrous operation.

The latching lever may be angled proximally relative to the hub body, such that the latching lever engages the front plate prior to the hub being axially seated against the front plate, such that the latching lever is deflected in a distal direction.

A first lock feature may be on the front plate and a second lock feature may be on the hub, which when engaged will resist, but not prohibit, rotation of the coaxial introducer cannula about the longitudinal axis.

The second lock feature may be positioned on or in the latching lever.

The first lock feature and the second lock feature may form a hole/protrusion arrangement or a magnetic arrangement.

The catch may be a set of slotted protrusions that protrude outwardly in a distal direction from the front plate. The slotted protrusions may have respective opposed slots which face in a direction away from the longitudinal axis. The hub body may have a cylindrical recess defining a side wall, wherein the latch is in the form of a set of tabs that extend radially inwardly toward the longitudinal axis from the side wall of the cylindrical recess of the hub body.

As used herein, "generally," and other words of degree are relative modifiers intended to indicate permissible variation from the characteristic so modified. It is not intended to be limited to the absolute value or characteristic which it modifies but rather possessing more of the physical or functional characteristic than its opposite, and approaching or approximating such a physical or functional characteristic.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy apparatus, comprising:
   a biopsy needle;
   a sample manifold coupled to the biopsy needle, the sample manifold having a receptacle and an insertion axis, the receptacle having an interior side wall and a mounting pin that is formed on the interior side wall and projects inwardly from the interior side wall toward the insertion axis; and
   a sample container configured for insertion into the receptacle, wherein the sample container includes a cap portion, a basket portion, and a hinge, wherein the cap portion is joined to the basket portion by the hinge, and wherein the sample container includes a mounting channel that is sized and positioned to engage and follow the mounting pin of the receptacle as the sample container is rotated;
   wherein the mounting channel has an open end and a closed end, and when the mounting pin of the receptacle is received in the open end of the mounting channel of the sample container, a rotation of the sample container causes the mounting pin to follow a spiral shape of the mounting channel toward the closed end.

2. The biopsy apparatus of claim 1, wherein the rotation of the sample container causes the mounting pin to pull the sample container along the insertion axis into the receptacle of the manifold, and wherein the mounting channel spirals an arcuate distance of less than one turn of the sample container.

3. The biopsy apparatus of claim 2, wherein the open end is positioned to receive the mounting pin of the sample manifold to provide a rotational orientation of the sample container relative to the receptacle of the sample manifold about the insertion axis.

4. The biopsy apparatus of claim 1, wherein the basket portion includes a floor, the floor having a concave interior surface and a plurality of holes, the plurality of holes allowing a vacuum to travel through the sample container to deliver a tissue sample from the biopsy needle onto the concave interior surface of the floor.

5. The biopsy apparatus of claim 1, wherein the hinge facilitates a pivot of one or both of the cap portion and the basket portion around the hinge between a closed position and an open position, the open position providing access to contents of the sample container.

6. The biopsy apparatus of claim 5, wherein when the sample container is in the closed position, a partial side wall of the cap portion overlaps a partial side wall of the basket portion to form a snap fit.

7. The biopsy apparatus of claim 5, wherein the cap portion of the sample container includes a lid and a partial side wall, the lid including a domed cap and an annular rim, the annular rim joining the domed cap to define an annular lip, wherein the mounting channel is formed in, and spirals around, the annular rim.

8. The biopsy apparatus of claim 7, wherein the domed cap is transparent or translucent to permit visual inspection of the contents of the sample container without having to remove the sample container from the receptacle of the manifold.

9. The biopsy apparatus of claim 8, wherein the domed cap includes a magnification feature.

10. The biopsy apparatus of claim 7, comprising a seal placed around the annular rim to provide a vacuum-tight seal between the sample container and the receptacle of the manifold.

11. The biopsy apparatus of claim 10, wherein the basket portion includes a floor, the floor having a concave interior surface and a plurality of holes, the plurality of holes allowing a vacuum to travel through the sample container to deliver a tissue sample from the biopsy needle onto the concave interior surface of the floor.

12. The biopsy apparatus of claim 1, wherein the cap portion and the basket portion of the sample container together define an aperture and an interior sample chamber, and wherein the biopsy needle includes a vacuum cannula having a proximal end portion that extends to the aperture to deliver, via vacuum, tissue samples from the biopsy needle into the interior sample chamber.

13. The biopsy apparatus of claim 12, wherein the aperture of the sample container is formed by a first semicircular aperture of the cap portion positioned adjacent a second semicircular aperture of the basket portion when the sample container is in a closed position.

* * * * *